US012656431B2

(12) United States Patent (10) Patent No.: US 12,656,431 B2
Harris et al. (45) Date of Patent: Jun. 16, 2026

(54) SYSTEM AND METHOD FOR OPERATION AND CONTROL OF ELECTROMAGNETS

(71) Applicant: SYNAPTIVE MEDICAL INC., Toronto (CA)

(72) Inventors: Chad Tyler Harris, Toronto (CA); Andrew Thomas Curtis, Ajax (CA)

(73) Assignee: SYNAPTIVE MEDICAL INC.

( * ) Notice: Subject to any disclaimer, the term of this patent is extended or adjusted under 35 U.S.C. 154(b) by 12 days.

(21) Appl. No.: 18/300,509

(22) Filed: Apr. 14, 2023

(65) Prior Publication Data

US 2023/0333181 A1 Oct. 19, 2023

Related U.S. Application Data

(60) Provisional application No. 63/362,986, filed on Apr. 14, 2022.

(51) Int. Cl.
| | |
|---|---|
| *G01V 3/00* | (2006.01) |
| *A61B 5/055* | (2006.01) |
| *G01R 33/385* | (2006.01) |
| *G01R 33/483* | (2006.01) |

(52) U.S. Cl.
CPC .......... *G01R 33/3852* (2013.01); *A61B 5/055* (2013.01); *G01R 33/4833* (2013.01)

(58) Field of Classification Search
CPC .. G01R 33/485; G01R 33/4828; G06T 11/008
USPC ....................................................... 324/309
See application file for complete search history.

(56) References Cited

U.S. PATENT DOCUMENTS

| | | | |
|---|---|---|---|
| 6,359,436 B1 | 3/2002 | Miyamoto | |
| 2002/0053906 A1* | 5/2002 | Yamazaki | ........ G01R 33/56518 |
| | | | 324/309 |
| 2006/0012365 A1 | 1/2006 | Werthner | |
| 2021/0055365 A1 | 2/2021 | Hoshiyama | |

OTHER PUBLICATIONS

Search Report issued by the Intellectual Property Office of Great Britain in relation to the corresponding GB2305543.7 dated Sep. 20, 2023, 1 page.
Combined Search and Examination Report issued by the Intellectual Property Office of Great Britain in relation to the corresponding GB2305543.7 dated Sep. 21, 2023, 1 page.
Search Report issued by the Intellectual Property Office of Great Britain in relation to the corresponding GB2305543.7 dated Sep. 20, 2023, 2 pages.

* cited by examiner

*Primary Examiner* — Walter L Lindsay, Jr.
*Assistant Examiner* — Frederick Wenderoth

(57) ABSTRACT

A system and method for compensation of radiofrequency (RF) spatial encoding misalignment errors due to gradient non-linearity in magnetic resonance imaging is described. The true magnetic field produced by the gradient coils in space are taken into account in order to encode the appropriate frequency band and offset of the RF pulse corresponding to the desired spatial encoding position and thickness. This method is applicable to any positionally (frequency) encoded radiofrequency (RF) pulses including slice or slab excitation pulses, inversion pulses, spin echo (refocusing) pulses and spatial saturation pulses.

20 Claims, 2 Drawing Sheets

SYSTEM AND METHOD FOR OPERATION AND CONTROL OF ELECTROMAGNETS

BACKGROUND

The field of the invention is systems and methods for magnetic resonance imaging ("MRI").

Magnetic resonance imaging (MRI) is generally performed with very strong static magnetic fields. The static magnetic field, referred to as the "main field" or "BO field", is responsible for polarizing nuclei and is required for imaging during nuclear magnetic resonance.

Traditional MRI utilizes three orthogonal magnetic fields, also known as gradient fields, in order to produce an image. These three fields are created by three distinct coils, known as gradient coils. Gradient coils are designed to produce linearly varying magnetic fields over the field of view. The magnetic fields produced by gradient coils in an MRI system are not perfectly linear in space due to the physical geometry of the gradient coils with respect to the imaging region of interest. In some regions, the gradient strength is larger in magnitude than desired, and in others it is smaller. Slice-selective RF pulses normally rely heavily on the linearity of the gradient fields in order to perform spatially selective interactions with the imaging sample. A technique used extensively in MRI such as exciting magnetization, refocuses a slice for spin echo imaging, and selectively saturates or inverts magnetization.

If a desired slice position and thickness are requested assuming a perfectly linear gradient field, yet the true field suffers from non-linearity, the actual slice affected will be thinner or thicker and shifted from its desired location. The change in thickness and shift depends on the local enhancement or reduction in the gradient strength at the desired slice location.

SUMMARY

A system and method for compensation of radiofrequency (RF) spatial encoding misalignment errors due to gradient non-linearity in magnetic resonance imaging is described. In our invention, the true magnetic field produced by the gradient coils in space is taken into account in order to encode the appropriate frequency band and offset of the RF pulse corresponding to the desired spatial encoding position and thickness.

This method is applicable to any positionally (frequency) encoded radiofrequency (RF) pulses. For example: slice/slab excitation pulses; inversion pulses; spin echo (refocusing) pulses; and spatial saturation pulses.

DETAILED DESCRIPTION

Described herein are systems and methods for designing and producing spatially encoded RF pulses.

Described herein are systems and methods for operating and controlling electromagnets in an MRI system. In particular, the present disclosure describes methods for designing and producing more accurate spatially encoded RF pulses, which, during magnetic resonance imaging, help increase system performance.

Figure 1:
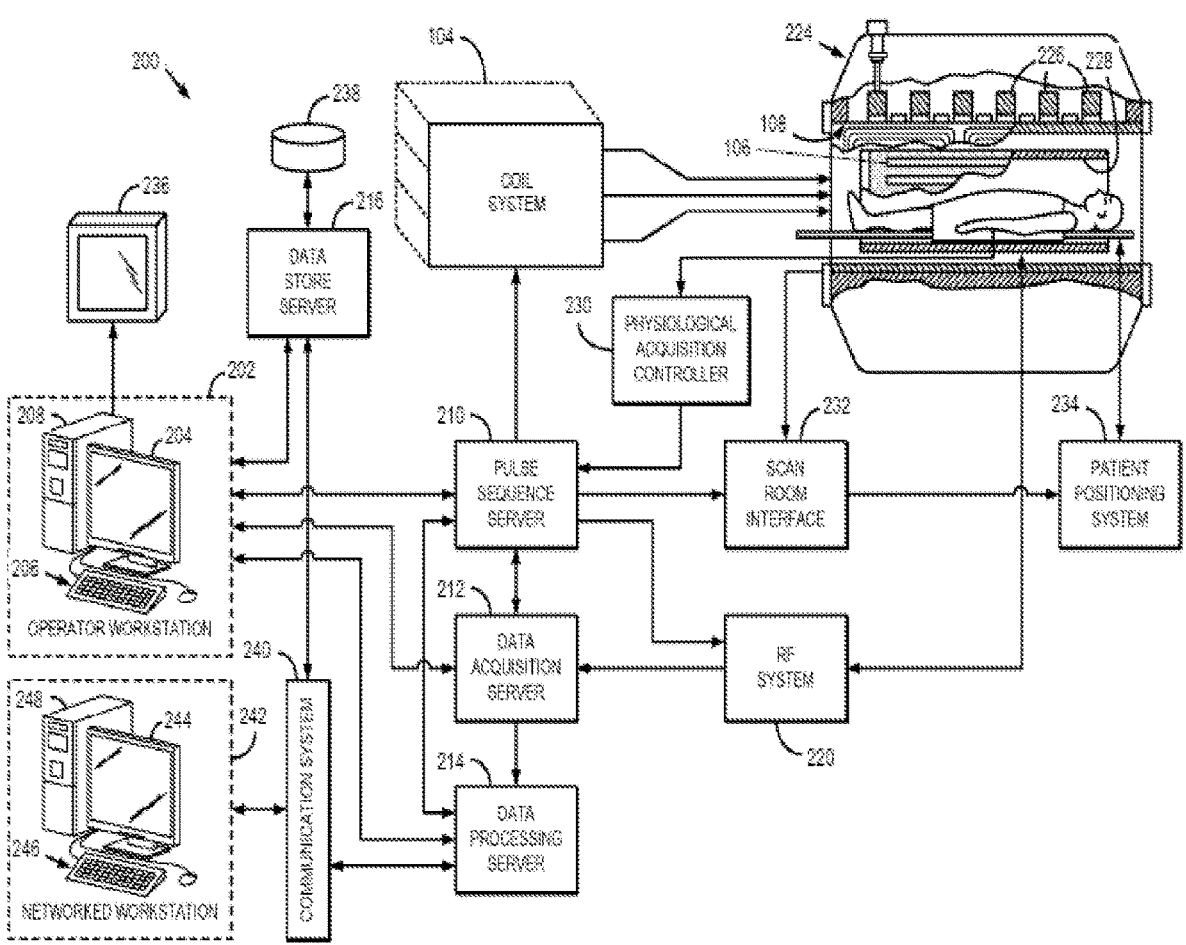
FIG. 1 is a block diagram of an example magnetic resonance imaging ("MRI") system, which incorporates an electromagnetic system.

FIG. 1 is a block diagram of an example magnetic resonance imaging ("MRI") system, which incorporates an electromagnetic system. According to FIG. 1, MRI system 200 includes an operator workstation 202, which will typically include a display 204; one or more input devices 206, such as a keyboard and mouse; and a processor 208. The processor 208 may include a commercially available programmable machine running a commercially available operating system. The operator workstation 202 provides the operator interface that enables scan prescriptions to be entered into the MRI system 200.

In general, the operator workstation 202 may be coupled to four servers: a pulse sequence server 210; a data acquisition server 212; a data processing server 214; and a data store server 216. The operator workstation 202 and each server 210, 212, 214, and 216 are connected to communicate with each other. For example, the servers 210, 212, 214, and 216 may be connected via a communication system 240, which may include any suitable network connection, whether wired, wireless, or a combination of both. As an example, the communication system 240 may include both proprietary or dedicated networks, as well as open networks, such as the internet.

The pulse sequence server 210 functions in response to instructions downloaded from the operator workstation 202 to operate a gradient system 218 and a radiofrequency ("RF") system 220. Gradient waveforms necessary to perform the prescribed scan are produced and applied to the gradient system 218, which excites gradient coils in an assembly 222 to produce the magnetic field gradients $G_x$, $G_y$, and $G_z$ used for position encoding magnetic resonance signals. The gradient coil assembly 222 forms part of a magnet assembly 224 that includes a polarizing magnet 226 and a whole-body RF coil 228.

RF waveforms are applied by the RF system 220 to the RF coil 228, or a separate local coil, in order to perform the prescribed magnetic resonance pulse sequence. Responsive magnetic resonance signals detected by the RF coil 228, or a separate local coil, are received by the RF system 220, where they are amplified, demodulated, filtered, and digitized under direction of commands produced by the pulse sequence server 210. The RF system 220 includes an RF transmitter for producing a wide variety of RF pulses used in MRI pulse sequences. The RF transmitter is responsive to the scan prescription and direction from the pulse sequence server 210 to produce RF pulses of the desired frequency, phase, and pulse amplitude waveform. The generated RF pulses may be applied to the whole-body RF coil 228 or to one or more local coils or coil arrays.

The RF system 220 also includes one or more RF receiver channels. Each RF receiver channel includes an RF preamplifier that amplifies the magnetic resonance signal received by the coil 228 to which it is connected, and a detector that detects and digitizes the quadrature components of the received magnetic resonance signal. The magnitude of the received magnetic resonance signal may, therefore, be determined at any sampled point by the square root of the sum of the squares of the components:

$$M = \sqrt{I^2 + Q^2} \qquad (1);$$

and the phase of the received magnetic resonance signal may also be determined according to the following relationship:

$$\varphi = \tan^{-1}\!\left(\frac{Q}{I}\right). \qquad (2)$$

The pulse sequence server 210 also optionally receives patient data from a physiological acquisition controller 230. By way of example, the physiological acquisition controller 230 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient to desired positions during the scan.

The digitized magnetic resonance signal samples produced by the RF system 220 are received by the data acquisition server 212. The data acquisition server 212 operates in response to instructions downloaded from the operator workstation 202 to receive the real-time magnetic resonance data and provide buffer storage, such that no data is lost by data overrun. In some scans, the data acquisition server 212 does little more than pass the acquired magnetic resonance data to the data processor server 214. However, in scans that require information derived from acquired magnetic resonance data to control the further performance of the scan, the data acquisition server 212 is programmed to produce such information and convey it to the pulse sequence server 210.

For example, during prescans, magnetic resonance data is acquired and used to calibrate the pulse sequence performed by the pulse sequence server 210. As another example, navigator signals may be acquired and used to adjust the operating parameters of the RF system 220 or the gradient system 218, or to control the view order in which k-space is sampled. In still another example, the data acquisition server 212 may also be employed to process magnetic resonance signals used to detect the arrival of a contrast agent in a magnetic resonance angiography ("MRA") scan. By way of example, the data acquisition server 212 acquires magnetic resonance data and processes it in real-time to produce information that is used to control the scan.

The data processing server 214 receives magnetic resonance data from the data acquisition server 212 and processes it in accordance with instructions downloaded from the operator workstation 202. Such processing may, for example, include one or more of the following:

reconstructing two-dimensional or three-dimensional images by performing a Fourier transformation of raw k-space data;
  performing other image reconstruction algorithms, such as iterative or back projection reconstruction algorithms;
  applying filters to raw k-space data or to reconstructed images;

generating functional magnetic resonance images;
  calculating motion or flow images; and so on.

Images reconstructed by the data processing server 214 are conveyed back to the operator workstation 202 where they are stored. Real-time images are stored in a data base memory cache, from which they may be output to operator display 212 or a display 236 that is located near the magnet assembly 224 for use by attending physicians. Batch mode images or selected real time images are stored in a host database on disc storage 238. When such images have been reconstructed and transferred to storage, the data processing server 214 notifies the data store server 216 on the operator workstation 202. The operator workstation 202 may be used by an operator to archive the images, produce films, or send the images via a network to other facilities.

The MRI system 200 may also include one or more networked workstations 242. By way of example, a networked workstation 242 may include a display 244; one or more input devices 246, such as a keyboard and mouse; and a processor 248. The networked workstation 242 may be located within the same facility as the operator workstation 202, or in a different facility, such as a different healthcare institution or clinic.

The networked workstation 242, whether within the same facility or in a different facility as the operator workstation 202, may gain remote access to the data processing server 214 or data store server 216 via the communication system 240. Accordingly, multiple networked workstations 242 may have access to the data processing server 214 and the data store server 216. In this manner, magnetic resonance data, reconstructed images, or other data may be exchanged between the data processing server 214 or the data store server 216 and the networked workstations 242, such that the data or images may be remotely processed by a networked workstation 242. This data may be exchanged in any suitable format, such as in accordance with the transmission control protocol ("TCP"), the internet protocol ("IP"), or other known or suitable protocols.

Referring to FIG. 1, there is illustrated a schematic of an electromagnet system 104 for use in a magnetic resonance imaging (MRI) system 200 during magnetic resonance imaging. The electromagnet system 104 comprises an orthogonal gradient set and may or may not include a high-order active shim set and/or a multi-coil array. The additional electromagnets (e.g. multi-coil array), may be placed within the same structure as the orthogonal gradient set or closer to the patient.

In our disclosure, the true magnetic field produced by the gradient coils in space are taken into account in order to excite the appropriate frequency band and offset corresponding to the desired excitation position and thickness.

For a given desired slice position z, and thickness t, the excitation frequency band and frequency offset assuming a perfectly linear gradient field is:

$$\Delta f = \frac{\gamma}{2\pi} Gt$$

$$f_{offset} = \frac{\gamma}{2\pi} Gz$$

where G is the nominal gradient strength.

However, if the true magnetic field produced by the gradient coil is used, the new frequency band and offset are given by:

$$\widetilde{\Delta f} = \frac{\gamma}{2\pi}\left[B_z\left(z+\frac{t}{2}\right) - B_z\left(z-\frac{t}{2}\right)\right]$$

$$\widetilde{f_{offset}} = \frac{\gamma}{4\pi}\left[B_z\left(z+\frac{t}{2}\right) + B_z\left(z-\frac{t}{2}\right)\right]$$

Where $B_z(x)$ is the magnetic field component along the axis of the main field produced by the gradient coils at a location x along the slice axis.

In the simple case of orthogonal excitations (i.e. axial, sagittal, and coronal), $B_z(x)$ is the field produced by the z-, x-, and y-gradient coils along the z-, x-, and y-axes respectively. However, for oblique slice planes, $B_z(x)$ is that produced by the linear combination of gradient coils needed to excite a slice along that axis and therefore, $B_z(x)$, is not confined to the field produced by a single gradient coil.

In one implementation, the desired excitation band and excitation offset are translated to an effective slice position and effective slice thickness, then communicated to the system as if they were the desired slice position and thickness. The effective slice position and effective slice thickness are computed as:

$$\tilde{z} = \frac{2\pi \widetilde{f_{offset}}}{\gamma G}$$

$$\tilde{t} = \frac{2\pi \widetilde{\Delta f}}{\gamma G}$$

Requesting the effective position and thickness compensates for the gradient non-linearity and produces a slice with the desired position and thickness. This new thickness can be achieved in a multitude of ways: by a combination of commanding a scaled version of the slice encoding gradient, and/or by designing an RF pulse with a different time bandwidth product.

In an application with a multi-slice or multi-slab acquisition, the set of slice locations to be imaged is typically given by the number of slices, a desired slice thickness, and the slice spacing (or gap). In that case, a compensated effective location and thickness can be computed separately for each slice location, yielding a more accurate set of imaging slices in space.

Figure 2:
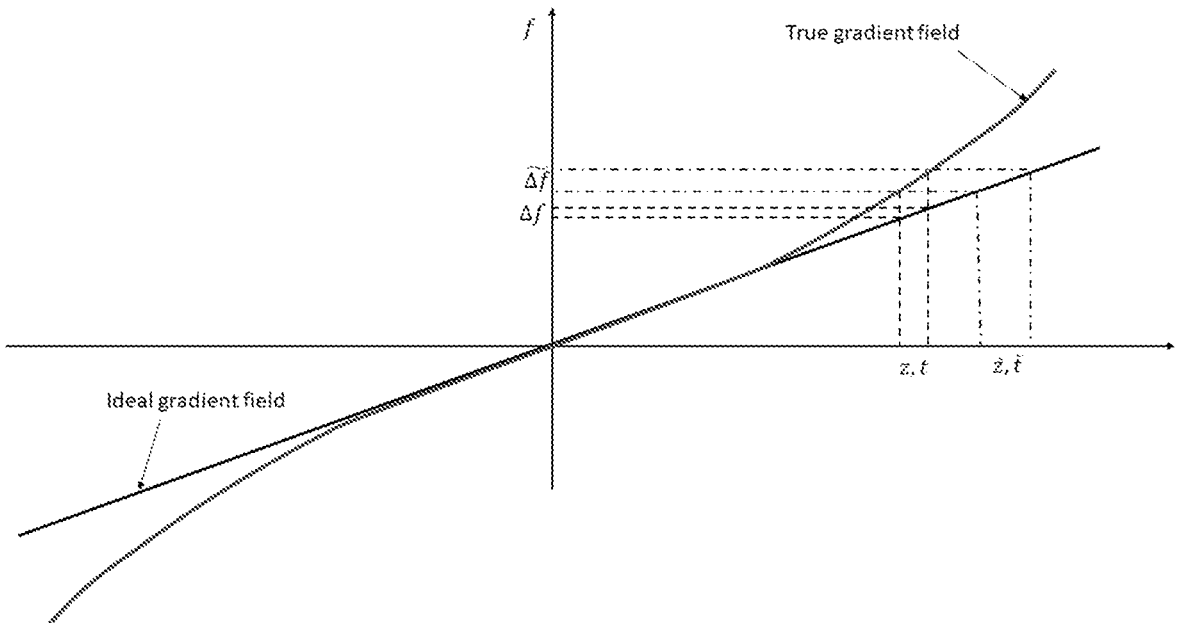
FIG. 2 displays the relationship between the desired slice position and thickness and the effective slice position and thickness for an example non-linear gradient field.

FIG. 2 displays the relationship between the desired slice position and thickness (z, t) and the effective slice position and thickness ($\tilde{z}$, $\tilde{t}$) for an example gradient non-linearity profile. In this example, the effective slice position is farther from isocenter than the desired slice position and the effective thickness is greater than the desired thickness. This is because the non-linearity in the gradient profile acts to increase the gradient strength. If the reverse were true, that is, the non-linearity acted to reduce the gradient strength, the effective slice position would be closer to isocenter than the desired position and the effective thickness would be smaller than the desired thickness.

Using the effective slice position and thickness in the pulse sequence design rather than the desired slice position and thickness results in greater spatial accuracy of the excited slice. That is, the excited slice position and thickness will be closer to the desired slice position and thickness.

In this embodiment, the pulse sequence would be unique to the particular gradient coil system installed in the scanner.

Therefore, the pulse sequence from one system with a given gradient coil electromagnetic design would not be directly translatable to another system with a different gradient coil electromagnetic design. Instead, a transformation would need to be done that would reverse any changes to the RF pulse design due to the first gradient model and apply changes due to the new gradient model.

Slice excitation is not the only use case for position (frequency) encoded RF pulses. This same problem and solution apply to many other pulse types, including inversion pulses, spin echo (refocusing) pulses, and spatial saturation pulses. In all cases, the same algorithm given above applies in order to correct for nominal slice location and offset.

According to the disclosure, a method for identification of frequency ranges for localization in a magnetic resonance imaging (MRI) device is disclosed. The method comprises the steps of determine the frequency bandwidth and frequency offset from a realistic spatially varying magnetic field over a slab in the x, y, and z axis and use the frequency bandwidth and frequency offset to improve spatial localization accuracy of MRI in the presence of non-linear gradient fields.

According to the disclosure, the slab of the method is a 3D rectangular prism oriented arbitrarily in space, with its three orthogonal axes labelled in the x, y and z axis. The z axis of the method is commonly referred to as the slab select axis and the improved spatial localization of the method is applied to slab excitation, inversion, refocusing, saturation, or other radiofrequency pulse applications.

According to the disclosure, the z axis is commonly referred to as the slab select axis and the improved spatial localization is applied to slab excitation, inversion, refocusing, saturation, or other radiofrequency pulse applications.

According to the disclosure, the realistic spatially varying magnetic field of the method is determined via an electromagnetic model of the gradient coil or via measurement of the gradient coil. The realistic spatially varying magnetic field of the method consists of a linear combination of multiple gradient coil profiles.

According to the disclosure, the frequency offset of the method is found by taking the average frequency computed with the realistic spatially varying magnetic field profile over an ideal 3D slab. The frequency bandwidth of the method is found by computing the spread in frequencies computed with the realistic spatially varying magnetic field profile over the ideal 3D slab.

According to the disclosure, the 3D ideal slab of the method is spatially constrained along the x and y axes. The spatial constraint of the 3D slab in the x and y directions of the method is determined at least in part by the object being imaged.

According to the disclosure, the spread in frequencies of the method is the standard deviation of the computed frequencies. The spread in frequencies of the method is the full width half max of the computed frequencies when plotted as a histogram.

According to the disclosure, the frequency offset of the method is found by taking the average frequency computed along the axis normal to an ideal slab in the z-axis over its 1D projection. The frequency offset of the method is found by taking the average frequency between the computed frequencies on the boundary of the 1D projection of the ideal slab.

According to the disclosure, the frequency bandwidth of the method is found by taking the range of frequencies between the computed frequencies on the boundary of the 1D projection of the ideal slab. The frequency bandwidth and frequency offset of the method are defined by an effective slab thickness and position, which are used in the pulse sequence design rather than the ideal slab thickness and position.

According to the disclosure, a system for identification of frequency ranges for localization in a magnetic resonance imaging (MRI) device is disclosed. The system comprises a processor, a set of magnet coils for generating a magnetic field, wherein the set of magnet coils are composed of a superconducting material, a set of gradient coils for generating linearly varying magnetic fields for imaging and a transmit RF coil for excitation of the nuclei.

According to the disclosure, the processor of the MRI system is configured to determine the the frequency bandwidth and frequency offset from a realistic spatially varying magnetic field over a slab in the x, y, and z axis, use the frequency bandwidth and frequency offset to improve spatial localization accuracy of MRI in the presence of non-linear gradient fields.

According to the disclosure, the slab of the system is a 3D rectangular prism oriented arbitrarily in space, with its three orthogonal axes labelled in the x, y and z axis. The z axis of the system is commonly referred to as the slab select axis and the improved spatial localization of the system is applied to slab excitation, inversion, refocusing, saturation, or other radiofrequency pulse applications.

According to the disclosure, the realistic spatially varying magnetic field of the system is determined via an electro-magnetic model of the gradient coil or via measurement of the gradient coil. The realistic spatially varying magnetic field of the system consists of a linear combination of multiple gradient coil profiles.

According to the disclosure, the frequency offset of the system is found by taking the average frequency computed with the realistic spatially varying magnetic field profile over an ideal 3D slab. Furthermore, the frequency bandwidth of the system is found by computing the spread in frequencies computed with the realistic spatially varying magnetic field profile over the ideal 3D slab.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read-only memory (ROM), volatile random access memory (RAM), non-volatile memory, cache or a remote storage device.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor. A "module" can be considered as a processor executing computer-readable code.

A processor as described herein can be a general-purpose processor, a digital signal processor (DSP), an application specific integrated circuit (ASIC), a field programmable gate array (FPGA) or other programmable logic device, discrete gate or transistor logic, discrete hardware components, or any combination thereof configured to perform the functions described herein. A general-purpose processor can be a microprocessor, but in the alternative, the processor can be a controller, or microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. In some embodiments, a processor can be a graphics processing unit (GPU). The parallel processing capabilities of GPUs can reduce the amount of time for training and using neural networks (and other machine learning models) compared to central processing units (CPUs). In some embodiments, a processor can be an ASIC including dedicated machine learning circuitry custom-build for one or both of model training and model inference. The disclosed or illustrated tasks can be distributed across multiple processors or computing devices of a computer system, including computing devices that are geographically distributed.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

The specific embodiments described above have been shown by way of example, and understood is that these embodiments may be susceptible to various modifications and alternative forms. Further understood is that the claims are not intended to be limited to the particular forms disclosed, but rather to cover all modifications, equivalents, and alternatives falling within the spirit and scope of this disclosure. While the foregoing written description of the system enables one of ordinary skill to make and use what is considered presently to be the best mode thereof, those of ordinary skill will understand and appreciate the existence of variations, combinations, and equivalents of the specific embodiment, method, and examples herein. The system should therefore not be limited by the above described embodiment, method, and examples, but by all embodiments and methods within the scope and spirit of the system. Thus, the present disclosure is not intended to be limited to the implementations shown herein but is to be accorded the widest scope consistent with the principles and novel features disclosed herein.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

We claim:

1. A computer-implemented method, using a computer processor in an operator workstation, for identification of frequency ranges for localization in a magnetic resonance imaging (MRI) device comprising the steps of:
   determine the frequency bandwidth and frequency offset, by the computer processor of the operator workstation, from a realistic spatially varying magnetic field over a slab in the x, y, and z axis; and
   use the frequency bandwidth and frequency offset to improve spatial localization accuracy of MRI in the presence of non-linear gradient fields;
   storing the improved spatial localization data in a database; and
   displaying the improved spatial localization data to an operator on an operator interface;
   wherein the slab is a 3D rectangular prism oriented arbitrarily in space, with its three orthogonal axes labelled in the x, y and z axis;
   wherein the z axis is commonly referred to as the slab select axis;
   wherein the improved spatial localization is applied to slab excitation, inversion, refocusing, saturation, or other radiofrequency pulse applications.

2. A system for identification of frequency ranges for localization in a magnetic resonance imaging (MRI) comprising:
   a computer processor;
   a set of magnet coils for generating a magnetic field, wherein the set of magnet coils are composed of a superconducting material;
   a set of gradient coils for generating linearly varying magnetic fields for imaging; and
   a transmit RF coil for excitation of the nuclei;
   wherein the processor of the MRI is configured to:
      determine the frequency bandwidth and frequency offset by the computer processor from a realistic spatially varying magnetic field over a slab in the x, y, and z axis;
      use the frequency bandwidth and frequency offset to improve spatial localization accuracy of MRI in the presence of non-linear gradient fields;

store the improved spatial localization data in a database; and
      display the improved spatial localization data to an operator on an operator interface;
   wherein the slab is a 3D rectangular prism oriented arbitrarily in space, with its three orthogonal axes labelled in the x, y and z axis,
   wherein the z axis is commonly referred to as the slab select axis;
   wherein the improved spatial localization is applied to slab excitation, inversion, refocusing, saturation, or other radiofrequency pulse applications.

3. The method of claim 1 wherein the realistic spatially varying magnetic field is determined via an electromagnetic model of the gradient coil.

4. The method of claim 1 wherein the realistic spatially varying magnetic field is determined via measurement of the gradient coil.

5. The method of claim 1 wherein the realistic spatially varying magnetic field consists of a linear combination of multiple gradient coil profiles.

6. The method of claim 1 wherein the frequency offset is found by taking the average frequency computed with the realistic spatially varying magnetic field profile over an ideal 3D slab.

7. The method of claim 1 wherein the frequency bandwidth is found by computing the spread in frequencies computed with the realistic spatially varying magnetic field profile over the ideal 3D slab.

8. The method of claim 1 wherein the frequency offset is found by taking the average frequency computed along the axis normal to an ideal slab in the z-axis over its 1D projection.

9. The method of claim 1 wherein the frequency offset is found by taking the average frequency between the computed frequencies on the boundary of the 1D projection of the ideal slab.

10. The method of claim 1 wherein the frequency bandwidth is found by taking the range of frequencies between the computed frequencies on the boundary of the 1D projection of the ideal slab.

11. The method of claim 1 wherein frequency bandwidth and frequency offset are defined by an effective slab thickness and position, which are used in the pulse sequence design rather than the ideal slab thickness and position.

12. The system of claim 2 wherein the realistic spatially varying magnetic field is determined via an electromagnetic model of the gradient coil.

13. The system of claim 2 wherein the realistic spatially varying magnetic field is determined via measurement of the gradient coil.

14. The system of claim 2 wherein the realistic spatially varying magnetic field consists of a linear combination of multiple gradient coil profiles.

15. The system of claim 2 wherein the frequency offset is found by taking the average frequency computed with the realistic spatially varying magnetic field profile over an ideal 3D slab.

16. The system of claim 2 wherein the frequency bandwidth is found by computing the spread in frequencies computed with the realistic spatially varying magnetic field profile over the ideal 3D slab.

17. The method of claim 7 wherein the 3D ideal slab is spatially constrained along the x and y axes.

18. The method of claim 7 wherein the spread in frequencies is the standard deviation of the computed frequencies.

19. The method of claim 7 wherein the spread in frequencies is the full width half max of the computed frequencies when plotted as a histogram.

20. The method of claim 17 wherein the spatial constraint of the 3D slab in the x and y directions is determined at least in part by the object being imaged.

* * * * *